US011805989B2

(12) United States Patent
Onobori

(10) Patent No.: US 11,805,989 B2
(45) Date of Patent: Nov. 7, 2023

(54) OPTICAL DISTRIBUTION CONNECTOR AND ENDOSCOPIC SYSTEM

(71) Applicant: HOYA CORPORATION, Tokyo (JP)

(72) Inventor: Kunihiko Onobori, Tokyo (JP)

(73) Assignee: HOYA CORPORATION, Tokyo (JP)

(*) Notice: Subject to any disclaimer, the term of this patent is extended or adjusted under 35 U.S.C. 154(b) by 386 days.

(21) Appl. No.: 17/052,394

(22) PCT Filed: Sep. 6, 2019

(86) PCT No.: PCT/JP2019/035272
§ 371 (c)(1),
(2) Date: Nov. 2, 2020

(87) PCT Pub. No.: WO2020/054634
PCT Pub. Date: Mar. 19, 2020

(65) Prior Publication Data
US 2021/0106211 A1 Apr. 15, 2021

(30) Foreign Application Priority Data
Sep. 13, 2018 (JP) ................................ 2018-171180

(51) Int. Cl.
*A61B 1/00* (2006.01)
*A61B 1/06* (2006.01)

(52) U.S. Cl.
CPC ........ *A61B 1/0638* (2013.01); *A61B 1/00006* (2013.01); *A61B 1/00045* (2013.01); *A61B 1/000095* (2022.02); *A61B 1/00117* (2013.01)

(58) Field of Classification Search
CPC ............ A61B 1/0638; A61B 1/000095; A61B 1/00006; A61B 1/00045; A61B 1/00117;
(Continued)

(56) References Cited

U.S. PATENT DOCUMENTS 4,283,115 A * 8/1981 Fraissl ................. G02B 27/145 600/165
4,600,831 A * 7/1986 Hutley ................. G11B 7/0908 250/201.4
(Continued)

FOREIGN PATENT DOCUMENTS

JP 08-106057 4/1996
JP 2003-038432 2/2003
(Continued)

OTHER PUBLICATIONS

Official Communication issued in International Bureau of WIPO Patent Application No. PCT/JP2019/035272, dated Dec. 3, 2019.
(Continued)

*Primary Examiner* — Timothy J Neal
*Assistant Examiner* — James Edward Boice
(74) *Attorney, Agent, or Firm* — GREENBLUM & BERNSTEIN, P.L.C.

(57) ABSTRACT

Provided is a technique for further reducing the scale of an endoscope system. An optical distribution connector according to the present disclosure discloses an optical distribution connector (additional connector) which includes an optical connector portion that is configured to be attachable to and detachable from a processor and realizes an optical connection with the processor, a plurality of medical device mounting portions, each of which is attachable to and detachable from a medical device, and at least one optical element that distributes light emitted from a light source included in the processor in each direction of the plurality of medical device mounting portions. In this optical distribution connector, at least one optical element has a spectral distribution wavelength characteristic defined by the light transmittance and the light reflectance for each of the plurality of wavelength bands of light (see FIG. 5).

6 Claims, 12 Drawing Sheets

(58) Field of Classification Search
CPC ......... A61B 1/06; A61B 1/07; A61B 1/00126; A61B 1/00059; G02B 23/24; G02B 23/26
USPC .......................................................... 600/160
See application file for complete search history.

(56) References Cited

U.S. PATENT DOCUMENTS 4,827,909 A * 5/1989 Kato ........................ A61B 1/05 600/166
5,617,302 A * 4/1997 Kloots ................. G02B 6/3604 362/581
6,048,349 A * 4/2000 Winston ................. A61B 1/042 606/15
2003/0142934 A1* 7/2003 Pan ...................... G01B 9/0205 385/116
2008/0084593 A1 4/2008 Horiguchi et al.
2009/0030278 A1* 1/2009 Minakuchi ............... A61B 1/05 600/118
2010/0134608 A1 6/2010 Shibasaki
2013/0012771 A1* 1/2013 Robertson .......... G02B 23/2469 600/104
2013/0041218 A1* 2/2013 Iida ...................... A61B 5/7257 600/109
2015/0138335 A1 5/2015 Kaminaga
2018/0120555 A1* 5/2018 Ikuta ..................... G01J 3/0205
2020/0154982 A1* 5/2020 Niwa ................. A61B 1/00126

FOREIGN PATENT DOCUMENTS

JP 2006-198103 8/2006
JP 2008-097748 4/2008
JP 2010-125270 6/2010
JP 2015-96912 5/2015
JP 2015-112208 6/2015
JP 2018-015282 2/2018

OTHER PUBLICATIONS

Office Action issued in Chinese Patent Application No. 201980033967.0, dated May 17, 2023.

* cited by examiner

A

B

X

OPTICAL ELEMENT CHANGING TRANSMITTANCE OF LIGHT

FIG. 10

TABLE 1. EXAMPLE OF OBSERVATION FUNCTION: OBSERVATION FUNCTION IS SAME IN PARENT-CHILE-GRANDCHILD DEVICES

| CONFIGURATION NAME | WHITE LIGHT | NARROWBAND OBSERVATION LIGHT | OXYGEN SATURATION OBSERVATION LIGHT | P-ZnPP | IR700 | ICG |
|---|---|---|---|---|---|---|
| PARENT SCOPE | 30% | 50% | 50% | 50% | 30% | 50% |
| CHILD SCOPE | 30% | 50% | 50% | 50% | 30% | 50% |
| GRANDCHILD SCOPE | 40% | 0% | 0% | 0% | 40% | 0% |
| WAVELENGTH BAND | UV — R1 | UV + G2 | A-1.UV + B2 + G2<br>A-2. | UV | R1 | R2 |

LIGHT ABSORPTION CHARACTERISTICS OF BLOOD HEMOGLOBIN

E1(422nm), E2(452nm), E3(502nm), E4(526nm)
E5(546nm), E6(570nm), E7(586nm), E8(620nm)

| BAND NAME | BAND [nm] | FIRST CORRESPONDING LIGHT SOURCE CONFIGURATION | SECOND CORRESPONDING LIGHT SOURCE CONFIGURATION | EMISSION BAND [nm] |
|---|---|---|---|---|
| W0 | 380−422 | UV | UV | 395−422 |
| W1 | 422−452 | B1 | B1 | 422−452 |
| W2 | 452−502 | B2 | B2 | 452−502 |
| W3 | 502−526 | G1 | G1 | 502−526 |
| W4−6 | 526−586 | G2 | G2 | 526−586nm |
| W7 | 586−620 | R1 | − | 586−620nm |
| WR | 620−800 | R2 | R1, R2 | R1: 675−705<br>R2: 765−805 |

OPTICAL DISTRIBUTION CONNECTOR AND ENDOSCOPIC SYSTEM

TECHNICAL FIELD

The present disclosure relates to an optical distribution connector and an endoscope system.

BACKGROUND ART

In recent years, in endoscope systems, two types of endoscope devices (scopes) have been connected so that various inspections and observations can be performed. For example, two endoscope devices with different diameters (a parent scope with a large scope diameter, and a child scope with a small scope diameter than that of the parent scope) are prepared to make it possible to observe the state of the affected area separately with both scopes.

Patent Literature 1 discloses an endoscope system in which two endoscope devices are used in combination, and in which a monitor and a VCR are shared. Further, in Patent Literature 1, a master mode in which the operation mode of one endoscope device operates the other endoscope device remotely, and a stand-alone mode in which the endoscope device operates without transmitting and receiving data with the other endoscope device are switched therebetween, so that the a device configuration is slimed.

CITATION LIST

Patent Literature

Patent Literature 1: JP 2003-38432 A

SUMMARY OF INVENTION

Technical Problem

However, in Patent Literature 1, it is necessary to separately prepare a light source and a processor for each endoscope device, and there is a problem that the scale of the endoscope system still becomes large.

The present disclosure has been made in view of such circumstances, and provides a technique for further reducing the scale of an endoscope system.

Solution to Problem

In order to solve the above-mentioned problems, this embodiment discloses an optical distribution connector (additional connector) which includes an optical connector portion that is configured to be attachable to and detachable from a processor and realizes an optical connection with the processor, a plurality of medical device mounting portions, each of which is attachable to and detachable from a medical device, and at least one optical element that distributes light emitted from a light source included in the processor in each direction of the plurality of medical device mounting portions. In this optical distribution connector, at least one optical element has a spectral distribution wavelength characteristic defined by the light transmittance and the light reflectance for each of the plurality of wavelength bands of light.

Further features related to the present disclosure will become apparent from the description of the present specification and the accompanying drawings. The present disclosure is achieved and implemented by elements and combinations of various elements and by modes of the following detailed description and the appended claims.

It is to be understood that the description in this specification is merely exemplary and is not intended to limit the significance of the claims or the application in any way.

Advantageous Effects of Invention

According to the present disclosure, it is possible to further reduce the scale of the endoscope system when using a plurality of medical devices at the same time.

BRIEF DESCRIPTION OF DRAWINGS

FIG. 4A illustrates a configuration example (first example) of the additional connector 200 that divides the light from the light source into two. FIGS. 4B and 4C illustrate configuration examples (second and third examples) of the additional connector 200 that divides the light from the light source into three.

FIG. 5A illustrates a configuration example of the additional connector 200 similar to that of FIGS. 4A-4C, and FIG. 5B illustrates the spectral distribution wavelength characteristic of the additional connector (distributor) 200.

FIG. 7A illustrates a configuration example of the additional connector 200, and FIG. 7B illustrates the spectral distribution wavelength characteristic of the additional connector (distributor) 200.

FIG. 10 is a diagram illustrating an example (Table 1) of an observation function in a case where the parent endoscope device (first medical device) 101, the child endoscope device (second medical device) 102, and the grandchild endoscope device (third medical device) 103 have the same observation function.

DESCRIPTION OF EMBODIMENTS

<External Configuration of Endoscope System>

Figure 1:
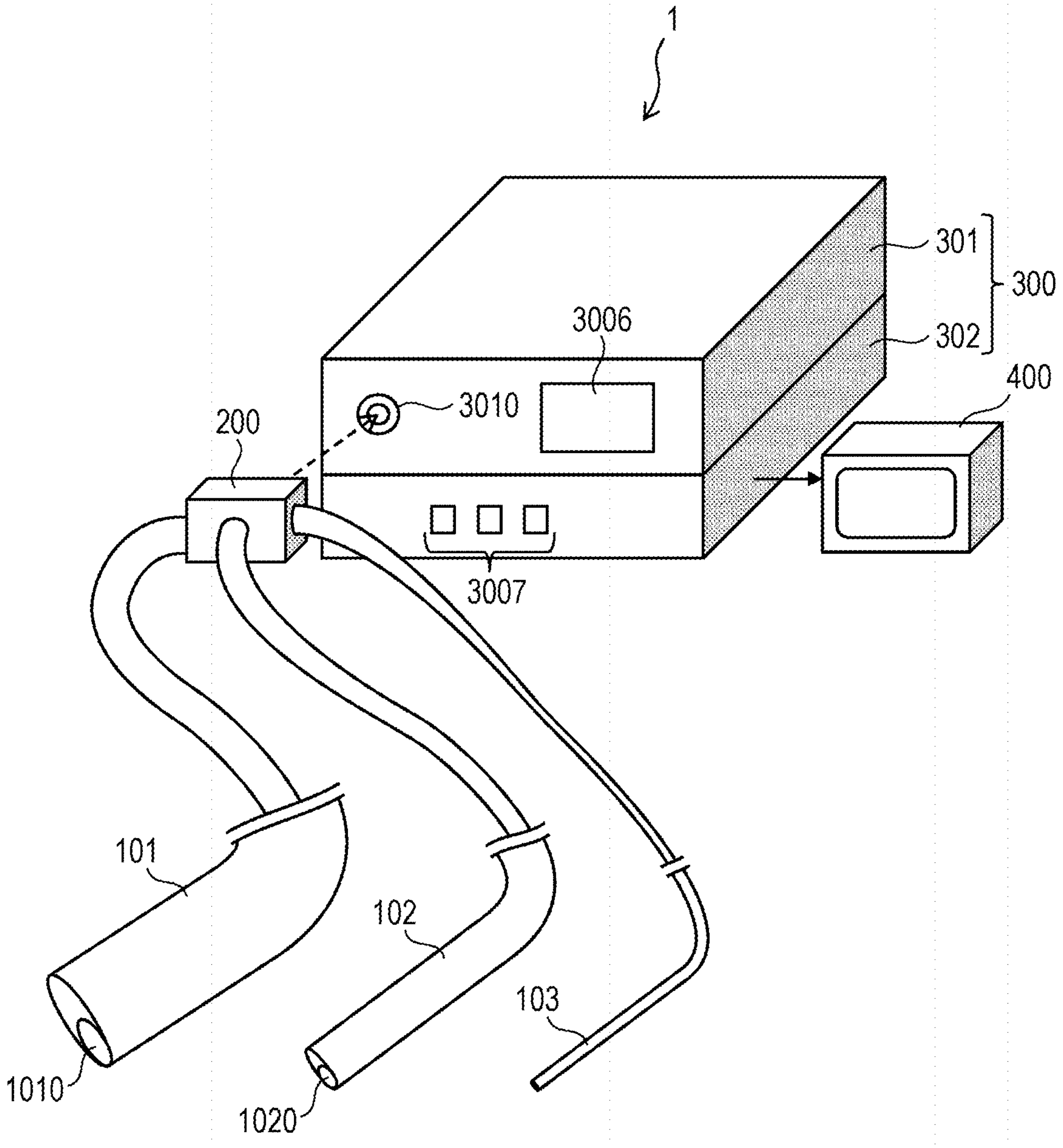
FIG. 1 is a diagram illustrating an external configuration example of an endoscope system 1 according to this embodiment.

FIG. 1 is a diagram illustrating an external configuration example of an endoscope system 1 according to this embodiment. As illustrated in FIG. 1, the endoscope system 1 includes a plurality of endoscope devices 101 to 103 (a parent endoscope device (corresponding to a first medical device) 101, a child endoscope device (corresponding to a second medical device) 102, and a grandchild endoscope device (corresponding to a third medical device) 103), an additional connector (hereinafter, also referred to as a "distributor" or an "optical distribution connector") 200, a processor 300, and a monitor 400. The additional connector 200 is attached to an optical connector portion 3010 on the processor 300 side, and the parent endoscope device 101, the child endoscope device 102, and the grandchild endoscope device 103 are connected to the processor 300 via the additional connector 200. The additional connector 200 has, for example, three connecting portions 201 to 203. For example, among the three, the parent endoscope device 101 formed of a normal tube having the largest diameter is connected to the connecting portion 201 of the additional connector 200, the child endoscope device 102 formed of a thin tube having an intermediate diameter is connected to the connecting portion 202, and the grandchild endoscope device 103 formed of an ultrafine tube having the smallest diameter is connected to the connecting portion 203.

The child endoscope device 102 is inserted from a forceps port (not illustrated) provided in the operation unit (not illustrated) of the parent endoscope device 101, and is passed through the forceps channel of the parent endoscope device 101. The child endoscope device 102 can be exposed from the forceps outlet 1010 of the distal end. In addition, similarly, the grandchild endoscope device 103 is inserted from a forceps inlet (not illustrated) provided in the operation unit (not illustrated) of the child endoscope device 102, and is passed through the forceps channel of the child endoscope device 102. The grandchild endoscope device 103 can be exposed from the forceps outlet 1020 of the distal end.

On the outer surface of the housing of the processor 300, there are provided an operation unit (operation panel) 3006 for an operator to input a predetermined instruction, an electrical connector portion 3007 for connecting the electric communication lines (lines for transmitting video signals, etc.) from the endoscope devices 101 to 103, and the optical connector portion 3010 which can directly connect each of the endoscope devices 101 to 103 and can attach the additional connector 200. Further, in FIG. 1, the electrical communication lines of the endoscope devices 101 to 103 and their connections are not illustrated, but in reality, the electrical communication lines of the endoscope devices 101 to 103 are connected to the electrical connector portion 3007. The electrical connector portion 3007 is configured by, for example, a port having a shape to which a USB or a circular connector can be connected. Further, FIG. 1 illustrates a state in which all of the parent endoscope device 101, the child endoscope device 102, and the grandchild endoscope device 103 are connected to the additional connector 200. However, all of the endoscope devices 101 to 103 are not necessary to be always connected. Any two endoscope devices may be connected depending on the application. Further, the processor 300 may be configured by separating a light source device 301 and a signal processing device 302.

Figure 2:
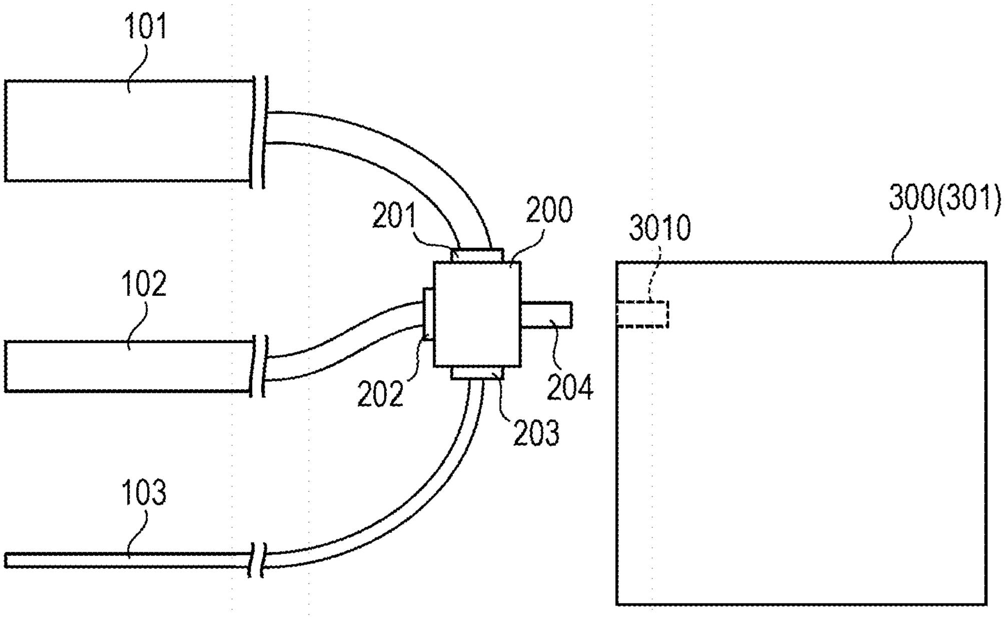
FIG. 2 is a top view illustrating a state in which a parent endoscope device 101, a child endoscope device 102, and a grandchild endoscope device 103 are connected to a processor 300 via an additional connector 200.

FIG. 2 is a top view illustrating a state in which the parent endoscope device 101, the child endoscope device 102, and the grandchild endoscope device 103 are connected to the processor 300 via the additional connector 200. As illustrated in FIG. 2, the endoscope devices 101 to 103 are connected to the connecting portions 201 to 203 of the additional connector 200 respectively, and a pin type connector (male) 204 of the additional connector 200 is inserted to the optical connector portion (connector hole (female)) 3010 of the processor 300 to complete the optical connection between the endoscope devices 101 to 103 and the processor 300. The connection order may be such that after the additional connector 200 is attached to the processor 300, the endoscope devices 101 to 103 are attached to the connecting portions 201 to 203 of the additional connector 200. Further, the additional connector 200 may have a contact hole structure, and the processor 300 may have a pin type connector (male) structure.

<Internal Configuration of Endoscope System>

Figure 3:
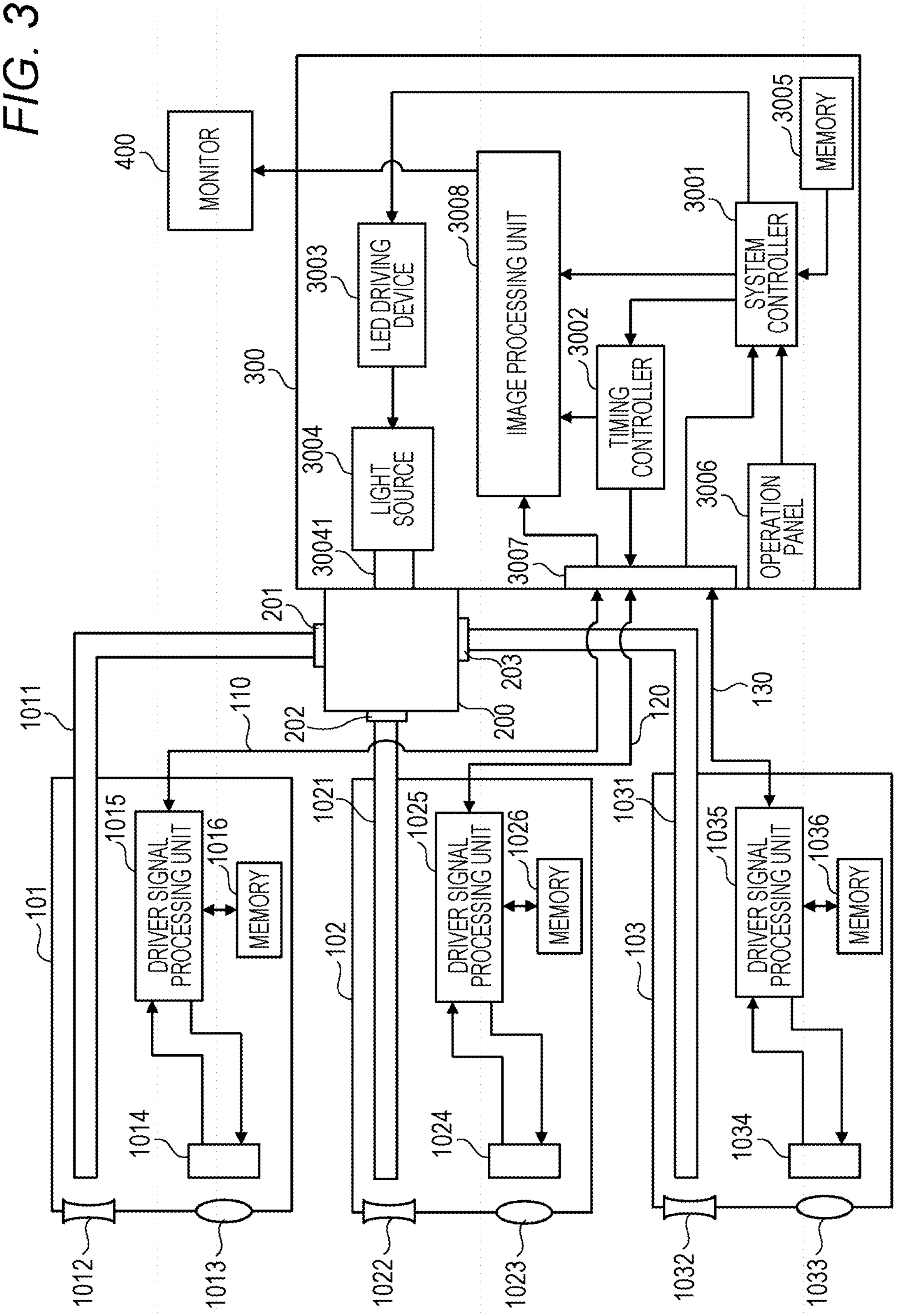
FIG. 3 is a diagram illustrating an internal configuration example of the endoscope system 1 when each of the endoscope devices 101 to 103 is attached to the processor 300 according to this embodiment.

FIG. 3 is a diagram illustrating an internal configuration example of the endoscope system 1 in a case where each of the endoscope devices 101 to 103 is attached to the processor 300 according to this embodiment. As illustrated above, the endoscope system 1 includes a plurality of endoscope devices 101 to 103 (the parent endoscope device (first medical device) 101, the child endoscope device (second medical device) 102, the grandchild endoscope device (third medical device) 103), the additional connector 200, the processor 300, and the monitor 400.

The processor 300 includes a system controller 3001, a timing controller 3002, an LED driving device 3003, the light source unit 3004, a memory 3005, an operation panel 3006, an electrical connector portion 3007, and an image processing unit 3008. The system controller 3001 executes various programs stored in the memory 3005 and integrally controls the entire endoscope system 1. The system controller 3001 is connected to an operation panel 3006. The system controller 3001 changes each of operation of the endoscope system 1 and parameters for each of the operation in accordance with an operator's instruction (user's instruction) input from the operation panel 3006. The timing controller 3002 outputs a clock pulse for adjusting the operation timing of individual units to individual processing units in the endoscope system 1.

The light source unit 3004 is configured by, for example, a plurality of LEDs (Light Emitting Diodes) (details will be described later), and emits irradiation light L 30041 after starting by the LED driving device 3003. In this embodiment, for example, the light source unit 3004 includes a plurality of LEDs, and each LED outputs light in a different wavelength band. Therefore, it is not necessary to generate the light of each wavelength band by the conventional optical filter. The light source unit 3004 is configured to, for example, adjust the intensity of light from each LED to be able to output, as the illumination light L 30041, white light (light including at least RGB components in the visible light band (380 nm to 780 nm)), 5-ALA (excitation light of PDD (Photodynamic-Diagnosis) using 5-aminolevulinic acid (for example, blue visible light (375 nm to 445 nm)), excitation light of PDT (Photodynamic-Therapy) using 5-ALA (for example, red visible light (600 nm to 740 nm) or green visible light (480 nm to 580 nm), and near-infrared light used in near-infrared immunotherapy (for example, a band light of 660 nm to 740 nm: since the peak of the absorption band of a substance called IRDye700 used in near-infrared immunotherapy is 689 nm, it is desirable that the light has a high light intensity of 680 to 700 nm). An image pickup device such as a CMOS image sensor described later is configured to receive the fluorescence of PDD using 5-ALA (fluorescence due to the excitation light: red fluorescence (600 to 740 nm), for example).

The endoscope system 1 of this embodiment is configured to be able to operate in three operation modes: a normal (white light) observation mode in which the white light generated by the light source unit 3004 is used as it is (or, removing the infrared components and/or ultraviolet components) as the illumination light (normal light (white light)) L 30041; a special observation mode in which the light (special light) having a predetermined wavelength band generated by the light source unit 3004 is used as the illumination light L 30041; and a baseline measurement mode for acquiring a correction value used in the special observation mode.

The illumination light L 30041 (normal light or special light) is split into a predetermined number of lights by the additional connector 200 (for example, white light is split into three, narrow band observation light is split into two, etc.: details will be described later), and introduced into each of LCBs (Light Carrying Bundles) 1011, 1021, and 1031 connected to the endoscope devices 101 to 103 respectively.

The irradiation lights L each introduced into the LCBs 1011, 1021, and 1031 propagate through the LCBs 1011, 1021, and 1031 emitted from the emission end faces of the LCBs 1011, 1021, and 1031 disposed at the tip from the endoscope devices 101 to 103, and applied to the object through light distribution lenses 1012, 1022, and 1032. The return light from the object illuminated by the irradiation light L forms an optical image on the light receiving surface of each of the solid-state imaging devices 1014, 1024, and 1034 via each of the objective lenses 1013, 1023, and 1033.

Further, each of the electric communication lines 110, 120, and 130 of the endoscope devices 101 to 103 is connected to an electrical connector portion 3007 of the processor 300, and each of the endoscope devices 101 to 103 is electrically connected to the processor 300. The video signals picked up by the endoscope devices 101 to 103 are supplied to the image processing unit 3008 of the processor 300 via the electric communication lines 110, 120, and 130 and the electrical connector portion 3007.

The solid-state imaging devices 1014, 1024, and 1034 are, for example, CMOS (Complementary Metal-Oxide-Semiconductor) image sensors or single-plate color CCD (Charge Coupled Device) image sensors having a Bayer type pixel arrangement. The solid-state imaging devices 1014, 1024, and 1034 accumulate the optical image formed by each pixel on the light receiving surface as electric charges according to the amount of light to generate and output an image signal (image data). The solid-state imaging devices 1014, 1024, and 1034 include an R filter that transmits red light, a G filter that transmits green light, and a B filter that transmits blue light, which are so-called on-chip color filters directly formed on the light receiving elements of the solid-state imaging devices 1014, 1024, and 1034. The image signals generated by the solid-state imaging devices 1014, 1024, and 1034 include an image signal R picked up by a light receiving device having the R filter, an image signal G picked up by a light receiving device having the G filter, and an image signal B picked up by a light receiving element having the B filter.

The solid-state imaging devices 1014, 1024, and 1034 are not limited to the CMOS image sensor and the CCD image sensor, and may be replaced with other types of image pickup devices.

As illustrated in FIG. 3, the endoscope devices 101 to 103 include driver signal processing units 1015, 1025, and 1035 respectively. An image signal is input to the driver signal processing unit 1015 from each of the solid-state imaging devices 1014, 1024, and 1034 in a field cycle. The driver signal processing units 1015, 1025, and 1035 perform predetermined processing on the image signals input from the solid-state imaging devices 1014, 1024, and 1034, and then output the image signals to the image processing unit 3008 of the processor 300.

The driver signal processing units 1015, 1025, and 1035 also access memories 1016, 1026, and 1036, respectively, and read the unique information of each of the endoscope devices 101 to 103. The unique information of each of the endoscope devices 101 to 103 recorded in the memories 1016, 1026, and 1036 includes, for example, the number of pixels, sensitivity, operable field rate, model number, and the like of the solid-state imaging devices 1014, 1024, and 1034. The driver signal processing units 1015, 1025, and 1035 output the unique information read from the memories 1016, 1026, and 1036 to the system controller 3001.

The system controller 3001 performs various calculations based on the unique information of the endoscope devices 101 to 103 and generates a control signal. The system controller 3001 controls the operation and timing of various processing units in the processor 300 using the generated control signal so as to perform processing suitable for the endoscope device connected to the processor 300.

The timing controller 3002 supplies a clock pulse to the driver signal processing units 1015, 1025, and 1035 in accordance with timing control by the system controller 3001. The driver signal processing units 1015, 1025, and 1035 each perform driving control of the corresponding solid-state imaging devices 1014, 1024, and 1034 at a timing synchronized with the field rate (frame rate) of the video image processed on the processor 300 side in accordance with the clock pulse supplied from the timing controller 3002.

The image processing unit 3008 performs predetermined signal processing such as color complementation, matrix calculation, Y/C separation, and the like on the image signals input from the driver signal processing units 1015, 1025, and 1035 in one field cycle. After that, screen data for monitor display is generated, and the generated screen data for monitor display is converted into a predetermined video format signal. The converted video format signal is output to the monitor 400. With this processing, an image of the object is displayed on a display screen of the monitor 400.

Further, the image processing unit 3008 may perform, for example, spectroscopic analysis processing based on the acquired image signals R (Red), G (Green), and B (Blue) in the special observation mode, calculate an index value having a correlation with an oxygen saturation degree in a biological tissue as an object, and generate image data for visually displaying the calculation result.

As described above, the endoscope system 1 of this embodiment is configured to operate in three modes: a normal observation mode in which the white light (normal light) emitted from the light source unit 3004 is used as the illumination light L 30041; a special observation mode in which the spectroscopic analysis is performed using the special light (the light of a specific wavelength band) emitted from the light source unit 3004 as the illumination light L 30041; and a baseline measurement mode for acquiring a correction value for special observation. Switching of each mode is performed by a user operation on an operation unit (not illustrated) of each of the endoscope devices 101 to 103 or the operation panel 3006 of the processor 300.

In the normal observation mode, the system controller 3001 controls the LED driving device 3003 to cause the light source unit 3004 to emit the white light (for example, light having a wavelength band of 400 nm to 770 nm). The emitted white light is split into three by the additional connector 200. Each of the split white lights is applied to the object (observation site) via the LCBs 1011, 1021, and 1031 of the endoscope devices 101 to 103. Reflected light obtained by reflecting the white light on the observation site is imaged by the solid-state imaging devices 1014, 1024, and 1034. The image data picked up by the solid-state imaging devices 1014, 1024, and 1034 is subjected to image processing as necessary, and then converted into a video signal and displayed on the monitor 400.

Figure 11:
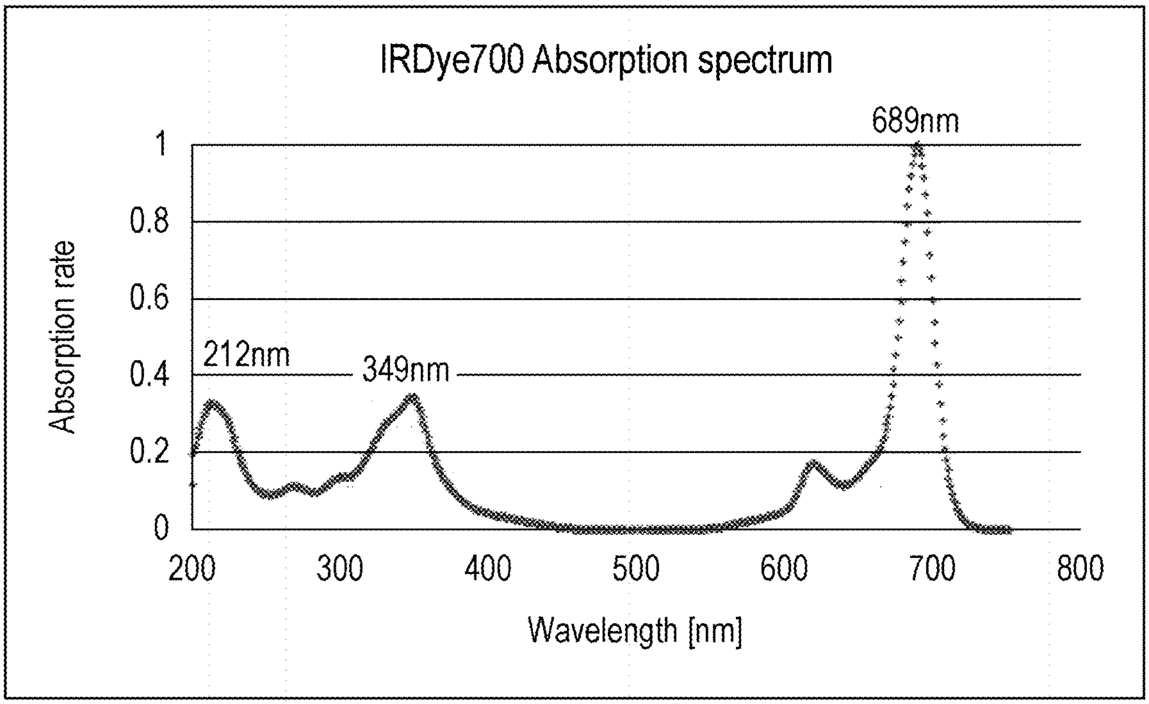
FIG. 11 is a diagram illustrating respective light absorption characteristics of IRDye700 and P-ZnPP.
Figure 11:
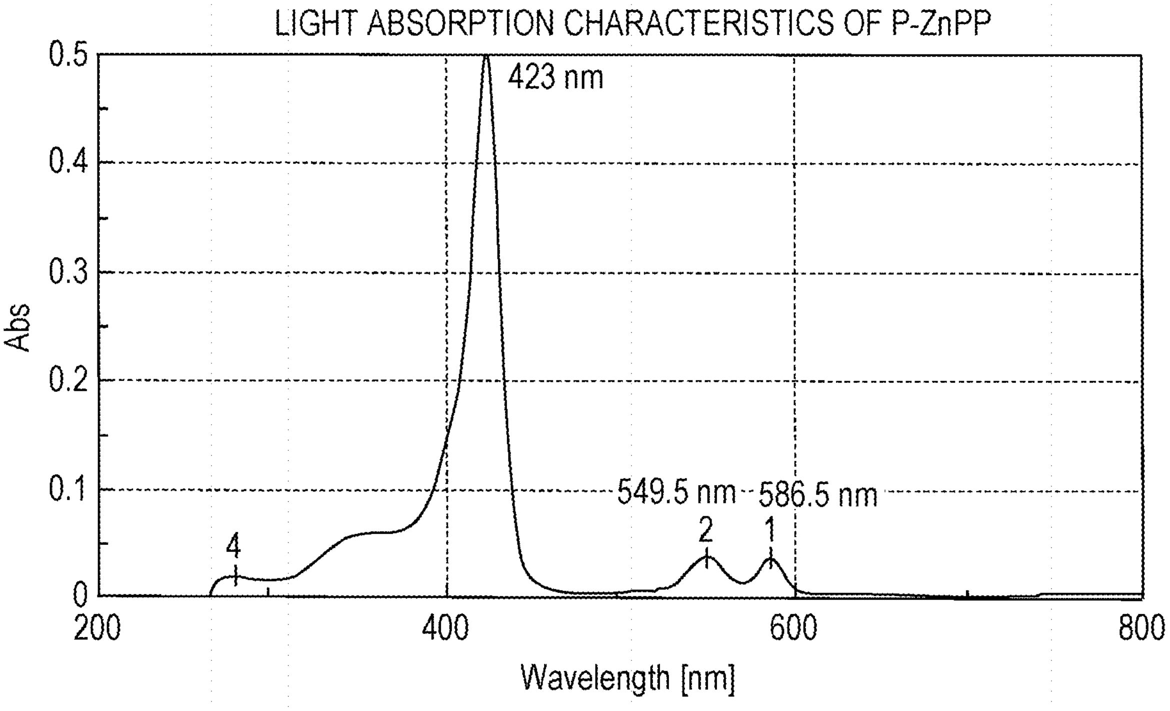

In the special observation mode and the baseline measurement mode, the system controller 3001 controls the LED driving device 3003 to cause the light source unit 3004 to emit the special light (for example, band light including light with central wavelengths of 415 nm and 530 nm (narrow band observation light), oxygen saturation observation light (band light of 526 to 585 nm, and band light of 546 to 570 nm: in the case of so-called Wide/Narrow method), P-ZnPP observation light (band light containing light with a wavelength of 423 nm), the light used in near-infrared immunotherapy (band light containing a light day with a wavelength of 689 nm (for example, near-infrared light containing the band from 660 to 740 nm)), and ICG observation light (band light containing light with 785 nm) (refer to FIG. 11 for P-ZnPP observation light and light used in near-infrared immunotherapy. In other words, in the case of P-ZnPP, it is necessary to emit the band light containing light of a wavelength of 423 nm, which has a peak light absorption characteristic, and in the case of near-infrared immunotherapy, it is necessary to emit the band light containing light of a wavelength of 689 nm which has a peak light absorption characteristic of IRDye700). The emitted special light is split into two or three by the additional connector 200. Each split special light is applied to the object (observation site) via the LCBs 1011, 1021, and 1031 of the endoscope devices 101 to 103. Reflected light obtained by reflecting the special light on the observation site is imaged by the solid-state imaging devices 1014, 1024, and 1034. The image data picked up by the solid-state imaging devices 1014, 1024, and 1034 is subjected to image processing as necessary, and then converted into a video signal and displayed on the monitor 400. In the special observation mode, a predetermined analysis process (for example, a depth-specific blood vessel traveling image generation process, a characteristic region specifying process, a blood transparentizing process, etc.) is performed based on the captured image data.

The baseline measurement mode is a mode in which the color reference plate such as an achromatic diffuser plate or a standard reflection plate is used as an object and is imaged under the illumination of the special light before the actual endoscope observation, and the data used for the standardization process of the special observation mode is acquired.

The image data R(x,y), G(x,y), and B(x,y) of the three primary colors imaged using special light in the baseline measurement mode are stored in an internal memory (not illustrated) of the image processing unit 3008 as baseline image data BLR(x,y), BLG(x,y), and BLB(x,y). Further, R(x,y), G(x,y), and B(x,y) and BLR(x,y), BLG(x,y), and BLB(x,y) are the values of the image data and baseline image data, respectively, of pixels (x,y). In addition, the pixel (x, y) is specified by the horizontal coordinate x and the vertical coordinate y.

<Basic Configuration Example of Additional Connector (Distributor)>

Figure 4:
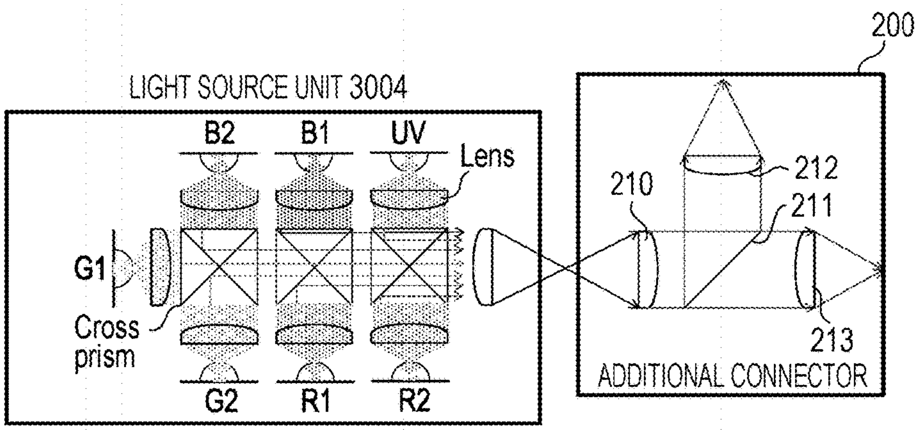
FIGS. 4A-4C are diagrams illustrating a schematic basic configuration example of an additional connector (distributor) according to this embodiment.
Figure 4:
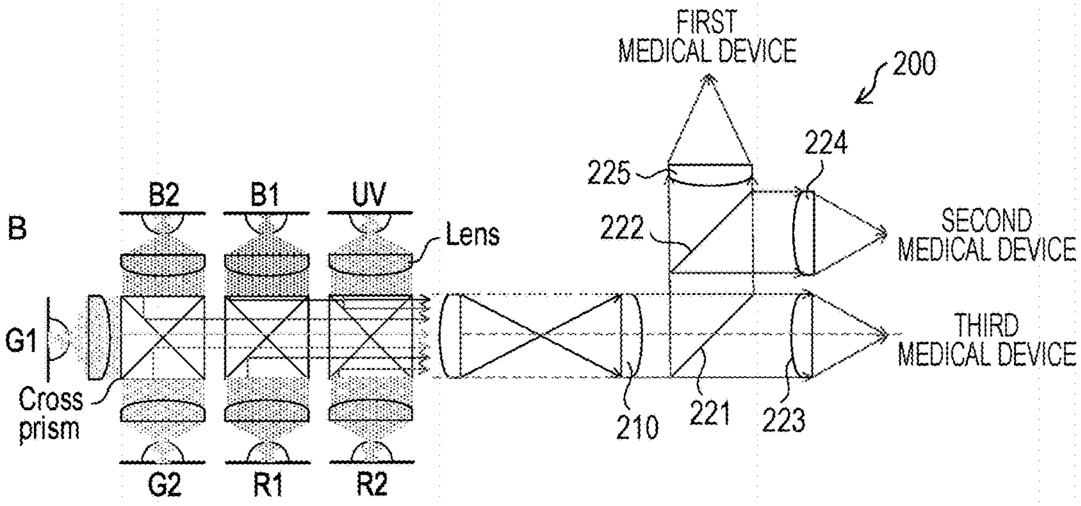
Figure 4:
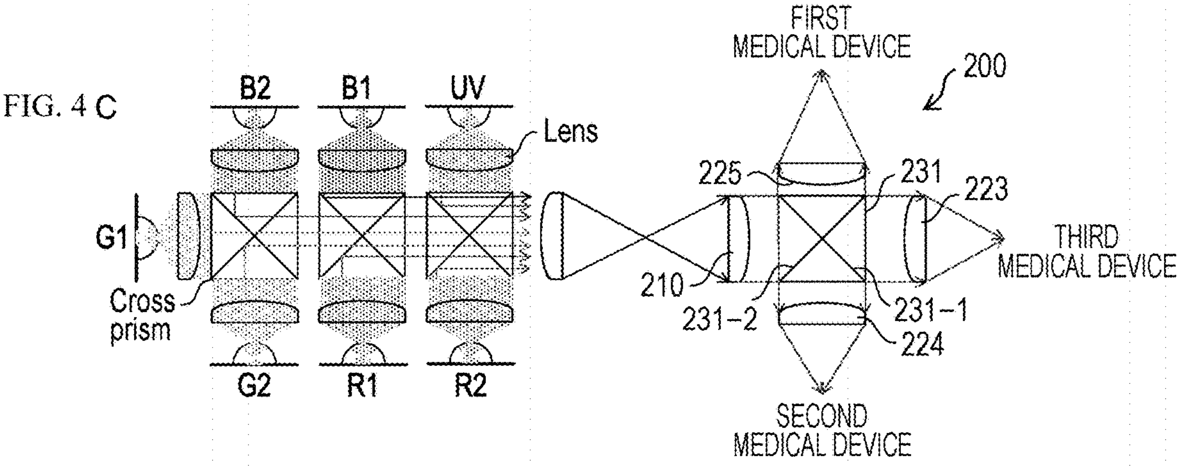

FIG. 4 is a diagram illustrating a schematic basic configuration example of the additional connector (distributor) according to this embodiment. FIG. 4A illustrates a configuration example (first example) of the additional connector 200 that divides the light from the light source into two. FIGS. 4B and 4C illustrate configuration examples (second and third examples) of the additional connector 200 that divides the light from the light source into three.

(i) First Example

As illustrated in FIG. 4A, the additional connector (distributor) 200 according to the first example includes an incident-side collimator lens 210 that optically adjusts (collimates) the light emitted from the light source unit 3004 into a parallel state, a dichroic mirror 211 that has a function of transmitting a part of the collimated light from the incident-side collimator lens 210 and reflecting the rest, a first emission-side collimator lens 212 that focuses the collimated light reflected by the dichroic mirror 211, and a second emission-side collimator lens 213 that focuses the collimated light passing through the dichroic mirror 211. The light transmittance and reflectance of the dichroic mirror 211 can be controlled to predetermined values by appropriately selecting a surface coating material. Further, it is possible to transmit or reflect light of a specific wavelength by devising the coating on the surface of the dichroic mirror 211. Since the adjustment of the optical characteristics of the dichroic mirror by coating the surface of the dichroic mirror is well known, it will not be described in detail here. Although the dichroic mirror is used in the first example, a half mirror may be used.

(ii) Second Example

As illustrated in FIG. 4B, the additional connector (distributor) 200 according to the second example includes the incident-side collimator lens 210 that optically adjusts (collimates) the light emitted from the light source unit 3004 into a parallel state, a first dichroic mirror 221 that has a function of transmitting and reflecting the collimated light from the incident-side collimator lens 210 at a predetermined ratio, a second dichroic mirror 222 that further transmits and reflects the light reflected on the dichroic mirror 211 at a predetermined ratio, a first emission-side collimator lens 223 that focuses the light passing through the first dichroic mirror 221, a second emission-side collimator lens 224 that focuses the light reflected on the dichroic mirror 222, and a third emission-side collimator lens 225 that focuses the light passing through the dichroic mirror 222. For example, if the transmittance of the first dichroic mirror 221 is set to 30%, the reflectance is set to 70%, and the transmittance and the reflectance of the second dichroic mirror 222 are each set to 50%, the distribution rate of the light by the additional connector 200 can be 30% for the third medical device, and 35% for the first and second medical devices.

(iii) Third Example

As illustrated in FIG. 4C, the additional connector (distributor) 200 according to the third example includes the incident-side collimator lens 210 that optically adjusts (collimates) the light emitted from the light source unit 3004 into a parallel state, a cross prism (cross dichroic prism) 231 that transmits and reflects the collimated light from the incident-side collimator lens 210 at a predetermined ratio and emits the light in three directions, the first emission-side collimator lens 223 that focuses the light passing through the cross prism 231, the second emission-side collimator lens 224 that focuses the light reflected on the lower side of the paper surface by the cross prism 231, and the third emission-side collimator lens 225 that focuses the light reflected on the upper side of the paper surface by the cross prism 231.

The cross prism 231 is an optical element that realizes the functions of two dichroic mirrors that transmit and reflect light in one. A prism boundary surface 231_1 transmits a predetermined ratio of the incident light and emits it to the third medical device, and reflects the remaining light to the first medical device (the upper side of the paper surface). Further, a prism boundary surface 231_2 transmits a predetermined ratio of the incident light and emits it to the third medical device, and reflects the remaining light to the second medical device (the lower side of the paper surface). Further, the transmittance and the reflectance can be adjusted by forming, for example, a light vapor deposition film on each of the prism boundary surfaces 231_1 and 231_2 of the cross prism 231. Further, the prism boundary surfaces (functional surfaces) 231_1 and 232_2 can be formed so that only light having a desired wavelength is transmitted and light having other wavelengths is reflected.

(iv) Light Source Unit

Figure 12:
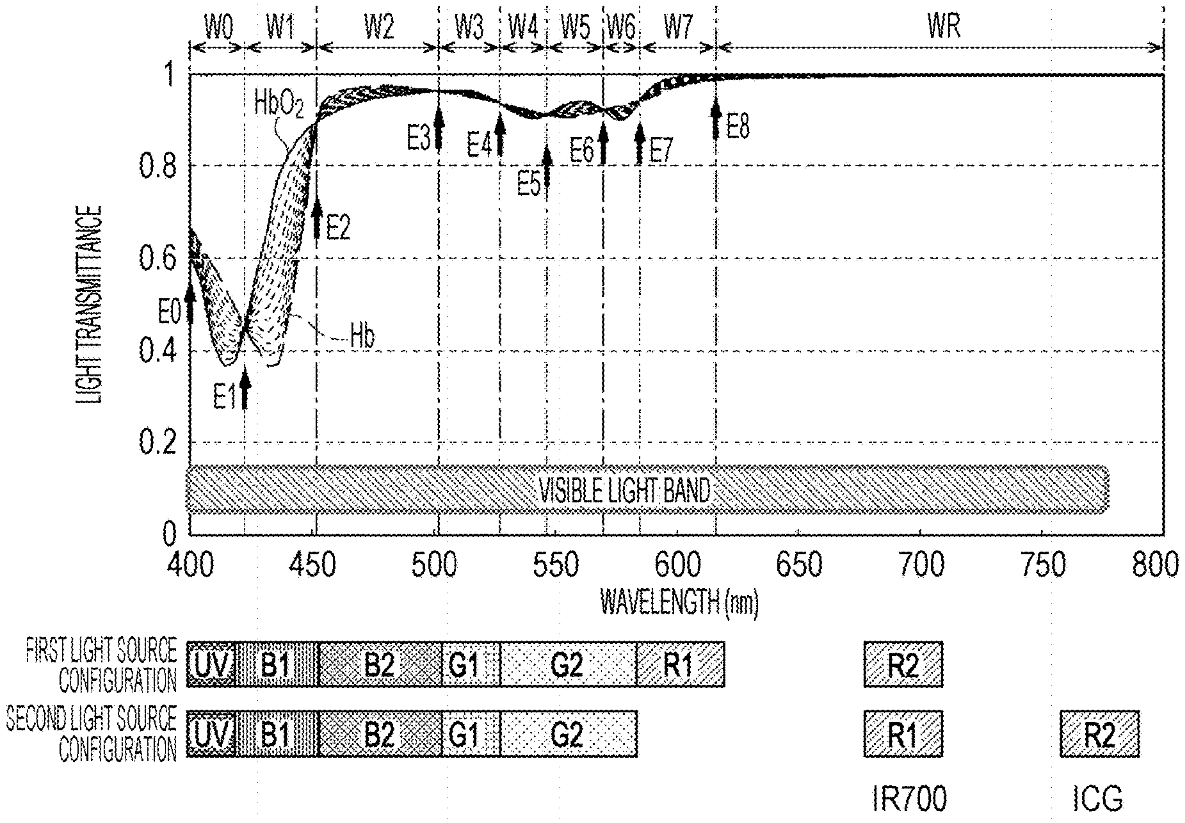
FIG. 12 is a diagram illustrating a light absorption characteristic of blood hemoglobin and a configuration example of a light source unit.
Figure 12:
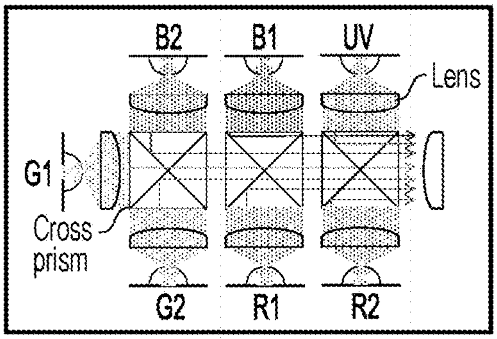

The light source unit 3004 may be configured by five LEDs that emit light of different wavelengths (LEDs that emit light of UV, B1, G1, G2, and R1 wavelengths), or seven LEDs that emit light of different wavelengths (for example, LEDs LED emitting light of UV (band light of 380 to 422 nm), B1 (band light of 422 to 452 nm), B2 (band light of 452 to 502 nm), G1 (band light of 502 to 526 nm), G2 (band light of 526 to 596 nm), R1 (band light of 586 to 620 nm), and R2 (band light of 620 to 800 nm). In this embodiment, the light source unit 3004 mounted with seven LEDs is illustrated, but the number of LEDs is not limited to seven. The light source unit 3004 may be configured by any number of LEDs such as five LEDs and three LEDs. Further, as illustrated in FIG. 12, even when seven LEDs are used, there are a plurality of types of light source units 3004.

(v) Collimator Lens

The focal lengths of the collimator lenses may be the same, or the transmittance and aberration of the surface filter may be changed according to the characteristics of light to be passed through the additional connector 200.

<Specific Configuration Example of Additional Connector (Distributor)>

Hereinafter, a specific configuration example of the additional connector (distributor) 200 will be described with reference to FIGS. 5 to 8.

(i) First Specific Configuration Example

Figure 5A:
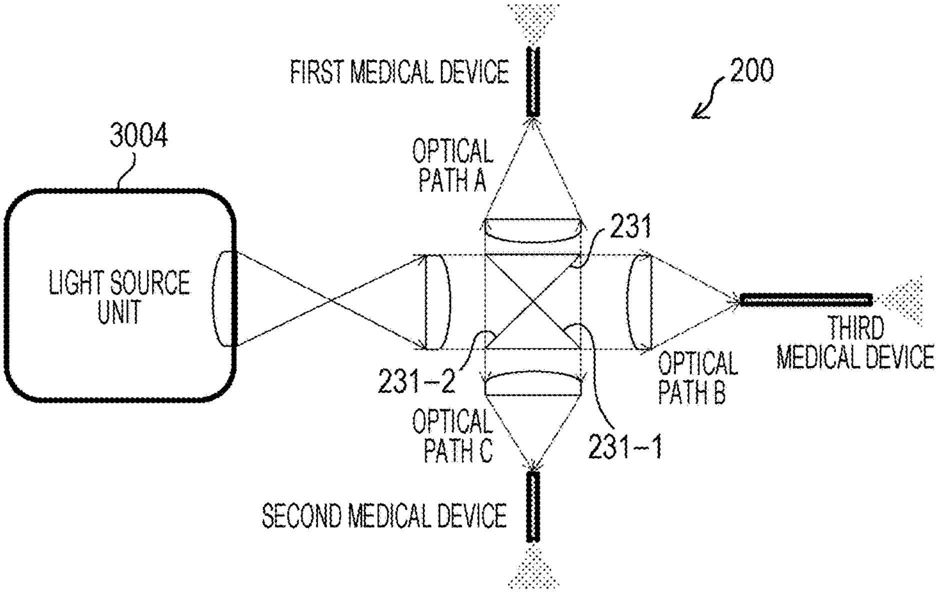
FIGS. 5A and 5B are diagrams for explaining a first specific configuration example of the additional connector (distributor) 200 according to this embodiment.
Figure 5B:
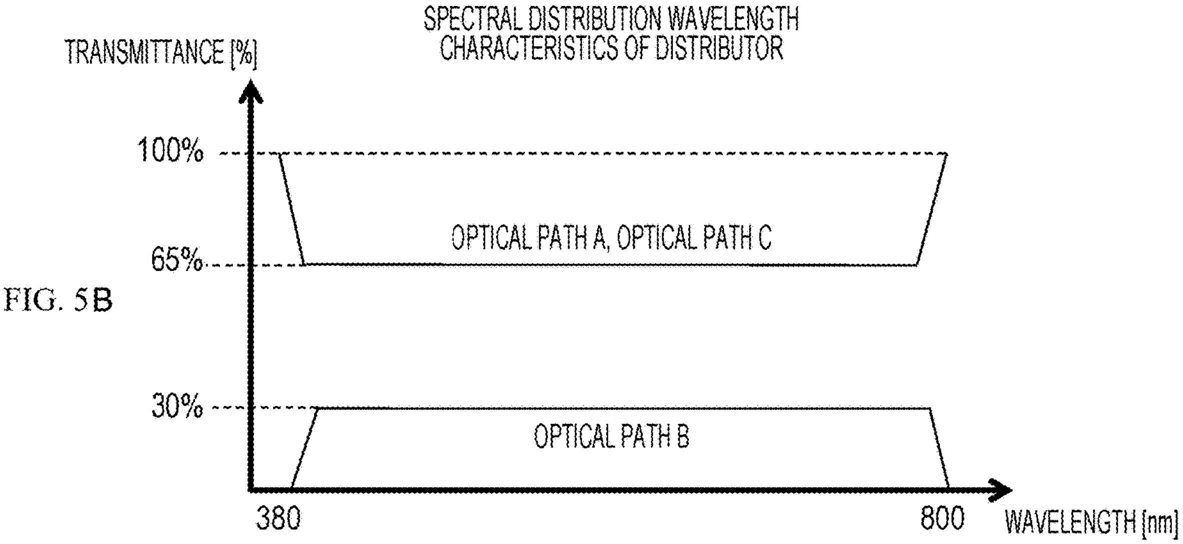

FIG. 5 is a diagram for explaining a first specific configuration example of the additional connector (distributor) 200 according to this embodiment. FIG. 5A illustrates a configuration example of the additional connector 200 similar to that of FIG. 4, and FIG. 5B illustrates the spectral distribution wavelength characteristic of the additional connector (distributor) 200. The internal configuration of the light source unit 3004 is the same as that illustrated in FIG. 4.

The additional connector 200 of FIG. 5A has the spectral distribution wavelength characteristic of FIG. 5B. The spectral distribution wavelength characteristic of the additional connector 200 is defined by the transmittance for an optical path B and the reflectance for optical paths A and C. Such spectral distribution wavelength characteristics are realized, for example, by coating (thin film coating) the prism boundary surfaces 231_1 and 231_2 of the cross prism 231 with a material suitable for exhibiting the optical characteristics. According to FIG. 5B, for example, with respect to the optical path B, the additional connector 200 transmits 30% of light (light having a wavelength of 380 nm to 800 nm) incident from the light source unit 3004 and outputs the light to the third medical device. Further, with respect to the optical paths A and C, the additional connector 200 reflects 35% of light incident from the light source unit 3004, and outputs the reflected light to the first and second medical devices, respectively.

(ii) Second Specific Configuration Example (Modification)

Figure 6:
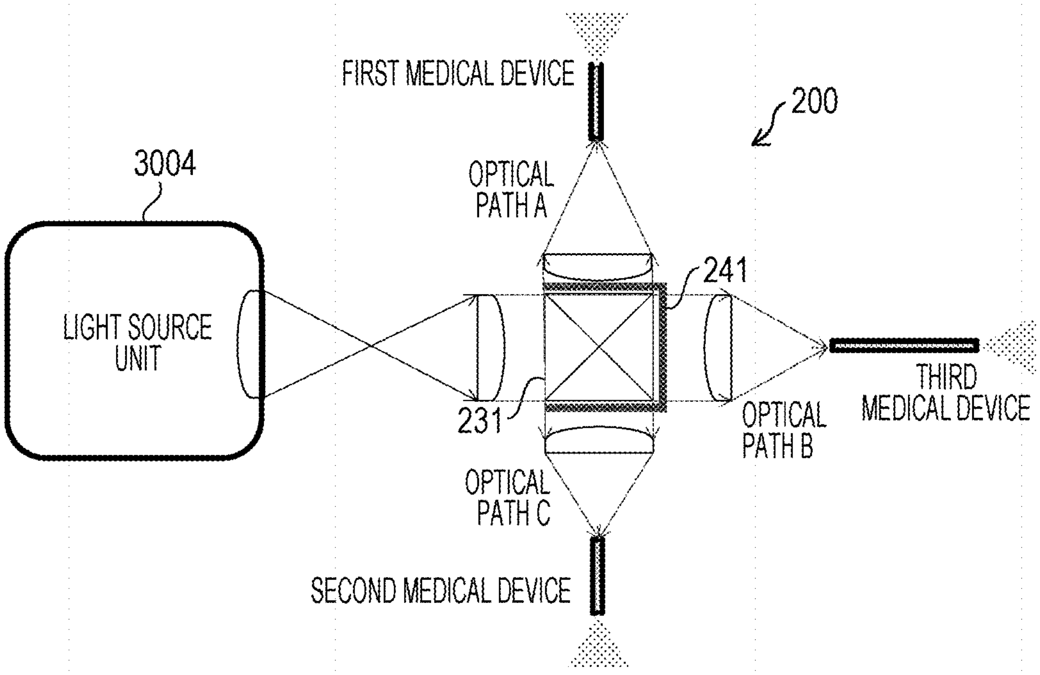
FIG. 6 is a diagram illustrating a second specific configuration example of the additional connector (distributor) 200.
Figure 6:
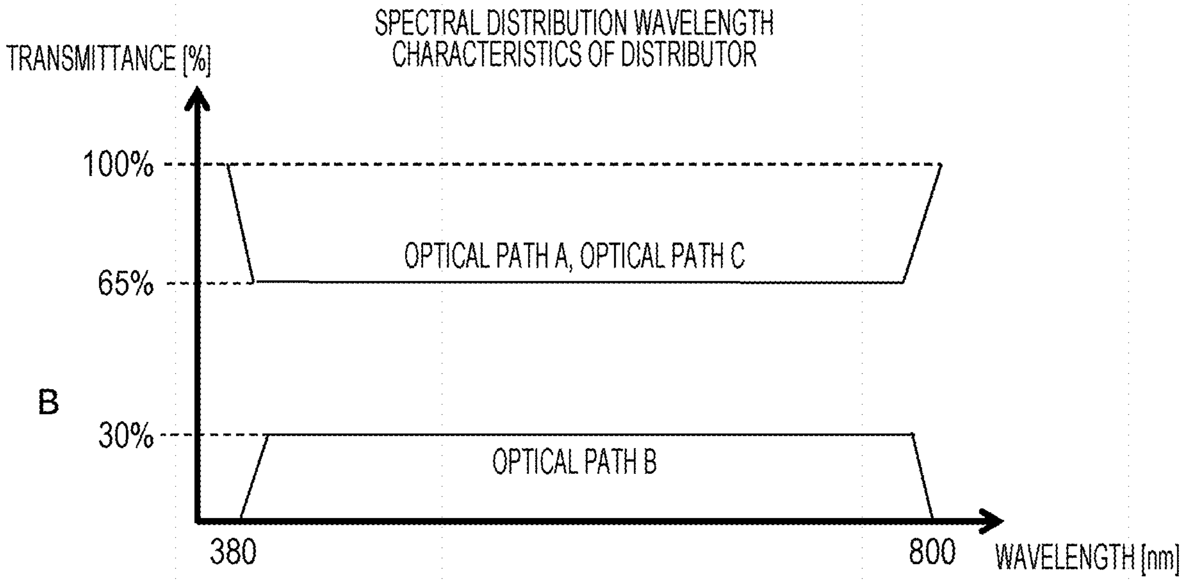

FIG. 6 is a diagram illustrating a second specific configuration example of the additional connector (distributor) 200. In addition to the configuration of the additional connector (distributor) 200 illustrated in FIG. 5, the additional connector (distributor) 200 illustrated in FIG. 6 includes an optical element 241 such as a liquid crystal tunable filter capable of changing the light transmittance. By using the optical element 241, it is possible to pass light in a wavelength-selective manner using a liquid crystal, and it is possible to select independent observation modes in the optical paths A, B, and C. For example, narrow-band light observation is possible on the optical paths A and C (only narrow-band observation light (415±10 nm and 530±10 nm) is transmitted), and the white light observation is possible on the optical path B (all visible light (for example, 400 nm to 770 nm) is transmitted).

(iii) Third Specific Configuration Example

Figure 7A:
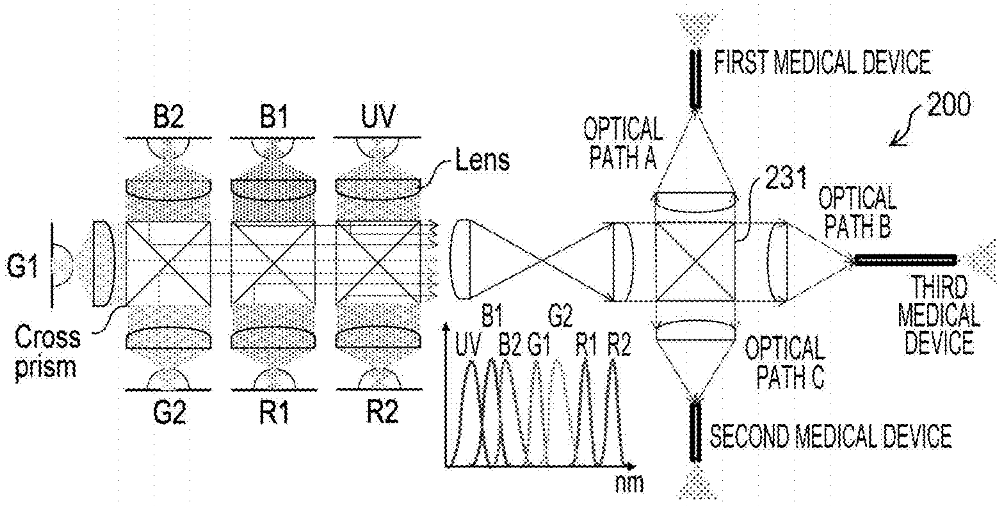
FIGS. 7A and 7B are diagrams illustrating a third specific configuration example of the additional connector (distributor) 200.
Figure 7B:
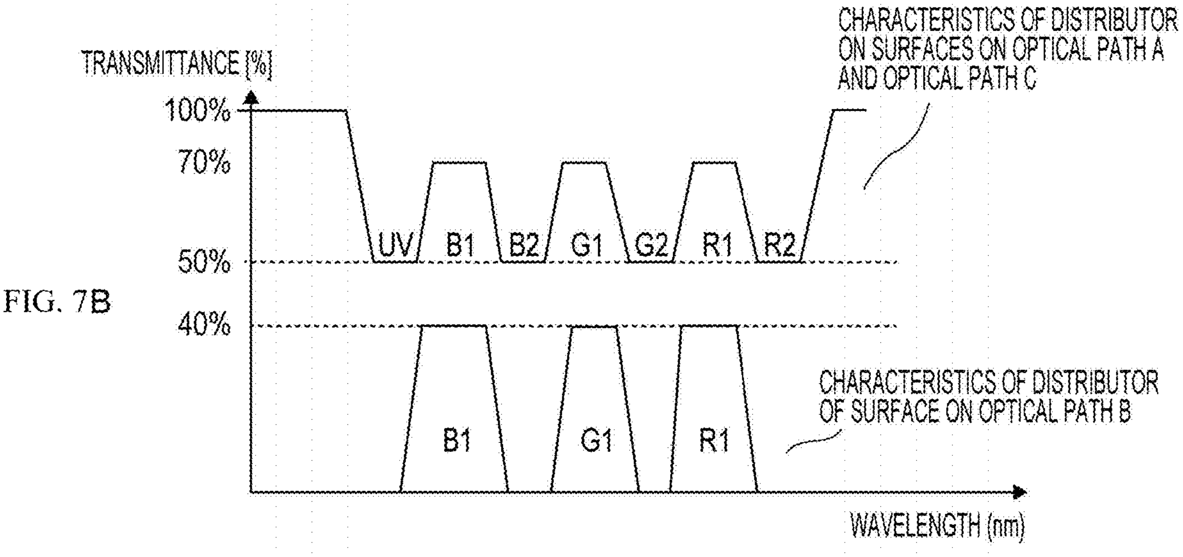

FIG. 7 is a diagram illustrating a third specific configuration example of the additional connector (distributor) 200. FIG. 7A illustrates a configuration example of the additional connector 200, and FIG. 7B illustrates the spectral distribution wavelength characteristic of the additional connector (distributor) 200. The difference between the additional connector 200 illustrated in FIG. 7 and the additional connector 200 illustrated in FIG. 5 is the spectral distribution wavelength characteristic of the cross prism 231.

In the spectral distribution wavelength characteristics in the third specific configuration example, as illustrated in FIG. 7B, 40% of B1 light, G1 light, and R1 light of the light incident from the light source unit 3004 (the light having wavelength bands of UV, B1, B2, G1, G2, R1, and R2) is transmitted and emitted on the optical path B to the third medical device. Further, the additional connector 200, with respect to the optical paths A and C, reflects 50% of UV light, B2 light, G2 light, and R2 light, and 30% of B1 light, G1 light, and R1 light of the lights (lights having the wavelength bands of B1, B2, G1, G2, R1, and R2) incident from the light source unit 3004, and emits the light to the first and second medical devices, respectively. By setting (fixed) the spectral distribution wavelength characteristic of the additional connector (distributor) 200 in the third specific configuration example as illustrated in FIG. 7B, the type of light emitted from the light source unit 3004 (the light of UV, B1, B2, G1, G2, R1, and R2) is selected, and the intensity of the light is controlled, so that it is possible to realize white light observation, narrow band light observation, oxygen saturation observation, P-ZnPP observation, treatment with near-infrared immunotherapy, and ICG observation. Hereinafter, the control in order to enable the respective observations on the light source unit 3004 will be described with reference to FIG. 8.

Figure 8:
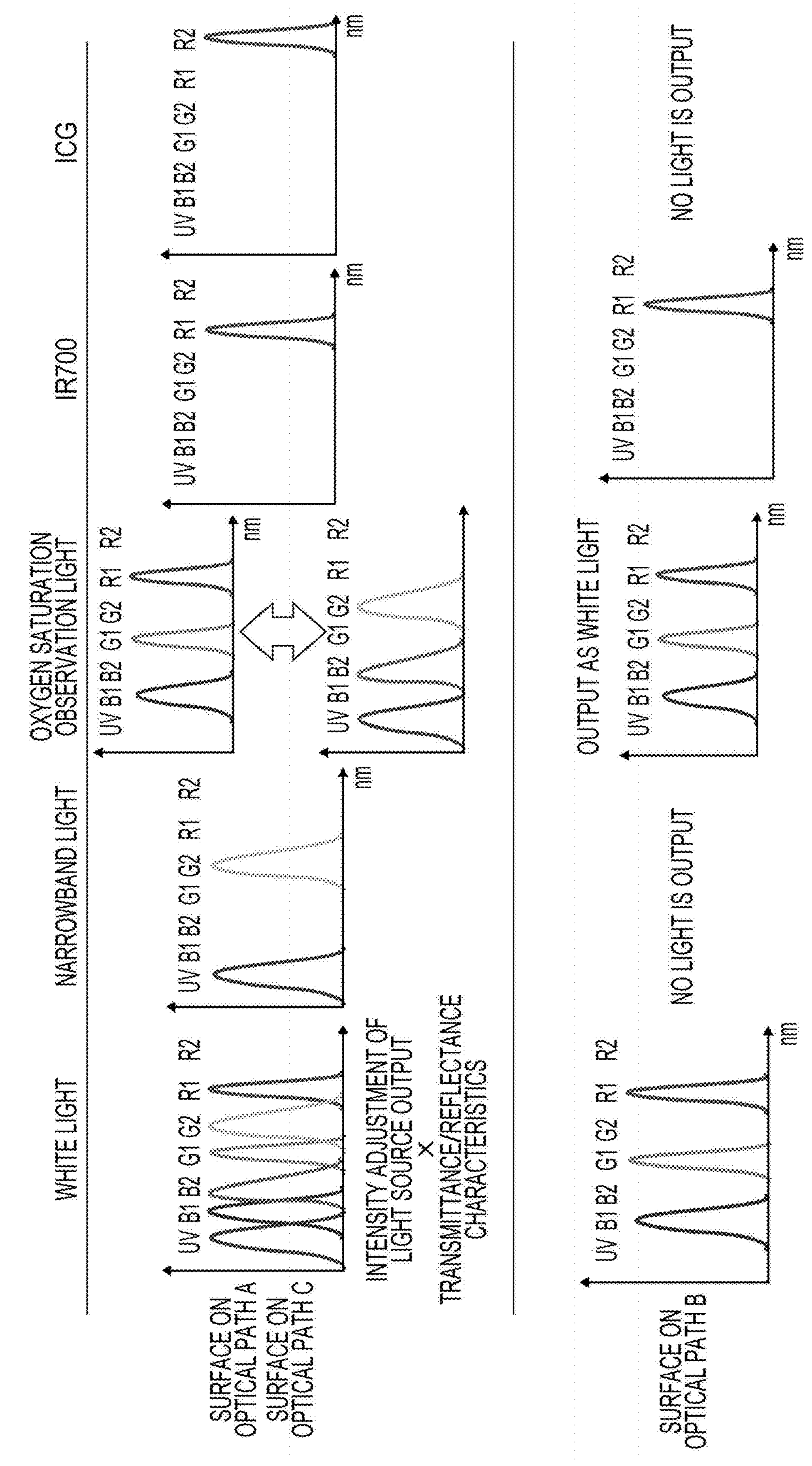
FIG. 8 is a diagram for explaining the control (wavelength band light selection and light intensity adjustment) of a light source unit 3004 when realizing white light, narrow band light, oxygen saturation observation light, light used in near-infrared immunotherapy, and ICG observation light using the additional connector (distributor) 200 having the spectral distribution wavelength characteristics illustrated in FIG. 7 FIGS. 7A and 7B.

FIG. 8 is a diagram for explaining the control (wavelength band light selection and light intensity adjustment) of the light source unit 3004 when realizing white light, narrow band light, oxygen saturation observation light, light used in near-infrared immunotherapy, and ICG observation light using the additional connector (distributor) 200 having the spectral distribution wavelength characteristics illustrated in FIG. 7.

(iii-1) White Light Generation

White light can be output from all optical paths from optical paths A to C. In this case, the light source unit 3004 drives 6 LEDs other than R2 out of seven LEDs (LEDs that emit light of wavelengths UV, B1, B2, G1, G2, R1, and R2) to output the light of the wavelength band from UV to R1. At this time, the intensity of each LED output is adjusted in consideration of the spectral distribution wavelength characteristics of the additional connector (distributor) 200 (FIG. 7B) and the light transmittance characteristics of the light guide from the additional connector (distributor) 200 to the tip of the medical device. Looking at the spectral distribution wavelength characteristics (FIG. 7B), UV light, B2 light, and G2 light are reflected by 50%, and B1, G1, and R1 light are reflected by 30% on the optical paths A and C. Further, according to the light transmittance characteristics of the light guide (see FIG. 9), the light transmittance of the light guide is lower than other wavelength bands up to around the wavelength band of 530 nm. Therefore, for example, the ratio of the intensity of B2 light and G2 light and the intensity of G1 light and R1 light is 3:5, the ratio of the intensity of UV light and the intensity of B1 light is 3:5, and the intensity of UV light is set to about 1.5 to 1.75 times the intensity of B2 light and G2 light, and the intensity of B1 light is set to about 1.5 to 1.75 times the intensity of G1 light or R1 light, so that it is possible to control the output intensity of each light from each optical path to be uniform. On the other hand, with respect to the optical path B, 40% of B1 light, G1 light, and R1 light is transmitted and output from the light source unit 3004. However, the ratio of the intensity of UV light to the intensity of B1 light (3:5) and the ratio of the intensity of UV light to the intensity of B2 light or G2 light (about 1.5 to 1.75 times) are just examples, and are not limited to this. However, the light source unit 3004 can be configured to output light adjusted so that the light emitted from the medical device has a desired RGB ratio.

Figure 9:
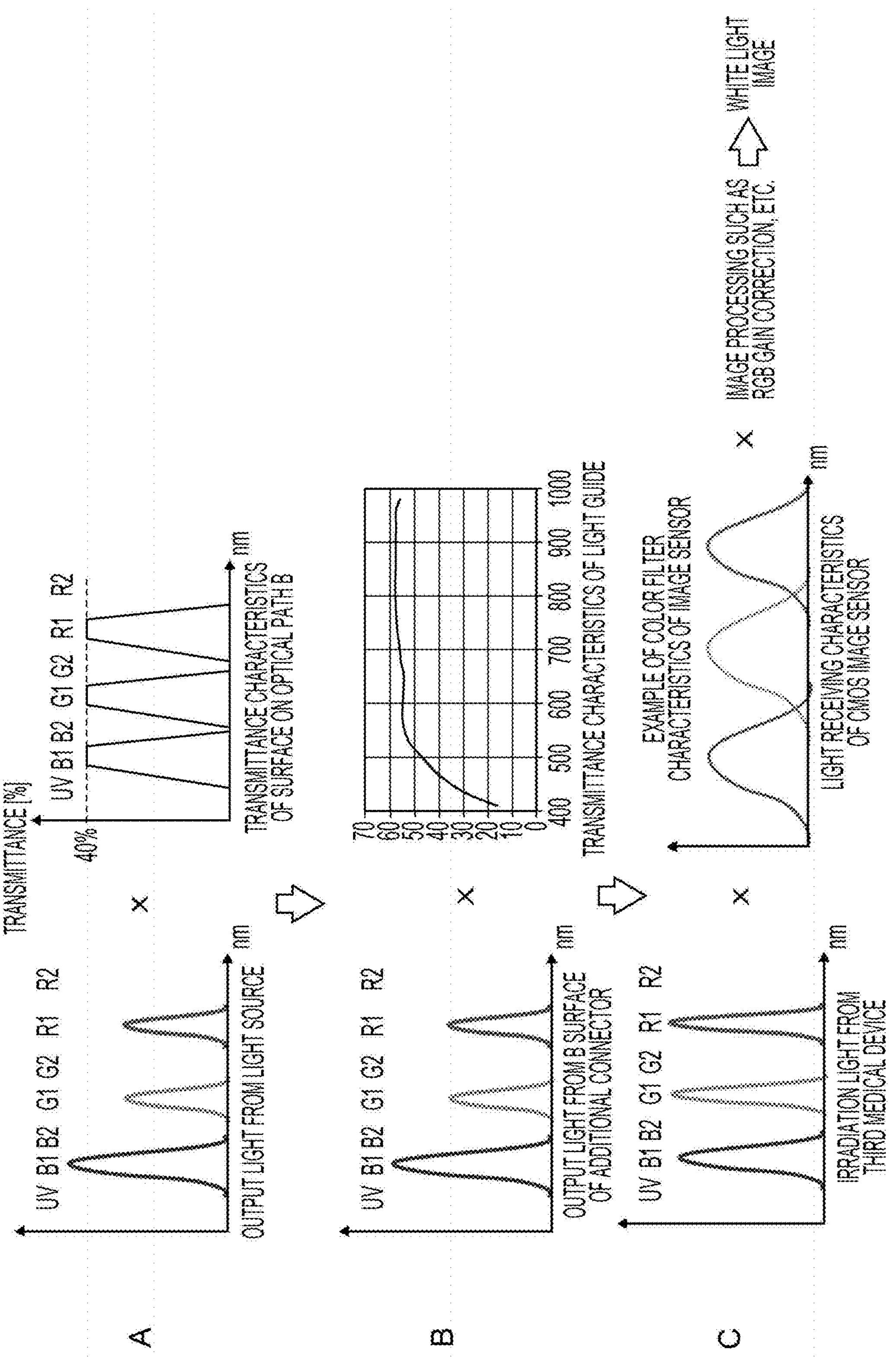
FIG. 9 is a diagram for explaining characteristics of light emitted from an optical path B and a flow of processing (outline) until a white image is output.

Here, the characteristics of the light emitted from the optical path B and the flow of processing (outline) until a white image is output will be described with reference to FIG. 9. Further, FIG. 9 illustrates only the processing steps for outputting white light to the optical path B, so the output light from the light source unit 3004 is illustrated as B1 light, G1 light, and R1 light. When the B1 light, G1 light, and R1 light output from the light source unit 3004 pass through the additional connector (distributor) 200 (FIG. 9A), 40% of B1 light, G1 light, and R1 light are output due to their spectral distribution wavelength characteristics (FIG. 7B) from the optical path B (FIG. 9B). In Step B, in the light output to the optical path B of the additional connector (distributor) 200, the B1 light has an intensity of about 1.5 to 1.75 times that of the G1 light and the R1 light (FIG. 9B). This is because the transmittance of the light guide of the third medical device connected to the optical path B is lower than other wavelength bands around 400 nm to 530 nm. That is, the B1 light, the G1 light, and the R1 light that have passed through the light guide and are output from the tip of the third medical device are emitted with substantially the same light intensity (FIG. 9C), and are applied to the observation target. The reflected light from the observation target is received by a solid-state image sensor (CMOS image sensor) 1034. As illustrated in FIG. 9C, the light receiving characteristics of the CMOS image sensor cover the bands of B1 light, G1 light, and R1 light reflected from the observation target, and the image of the observation target is captured by the solid-state image sensor 1034. Then, the image data captured and acquired is transferred to the image processing unit 3008 via the electrical connector portion 3007 of the processor 300. The image processing unit 3008 considers that the reflectance of RGB varies depending on the type of the observation target, and uses a look-up table to correct the RGB gain of the image data (adjusting the color balance (white balance)) to obtain a white light image, and outputs it as a white light image (displaying it on the screen) (FIG. 9C).

(iii-2) Narrow Band Light Generation

Narrowband light can be output from optical paths A and C. In this case, the light source unit 3004 drives two LEDs (LEDs emitting the wavelength bands of UV and G2, respectively) to output UV light (for example, 415±10 nm light) and G2 light (for example, 530±10 nm light). At this time, since the spectral distribution wavelength characteristics (FIG. 7B) of the additional connector (distributor) 200 are set to the same reflectance for UV light and G1 light, intensity is not adjusted based on the spectral distribution wavelength characteristics. However, the intensity of each LED output is adjusted in consideration of the light transmittance characteristics of the light guide from the additional connector (distributor) 200 to the tips of the first and second medical devices. According to the light transmittance characteristics of the light guide (see FIG. 9), the light transmittance of the light guide is lower than other wavelength bands up to around the wavelength band of 530 nm. Therefore, the intensity of UV light is set to about 1.5 to 1.75 times the intensity of G2 light.

On the other hand, since only B1 light, G1 light, and R2 light can pass through the optical path B (40% transmittance), no light is output from the optical path B.

(iii-3) Oxygen Saturation Observation Light Generation

The oxygen saturation observation light is output from the optical paths A and C, and the white light is output from the optical path B. In this case, the light source unit 3004 can alternately output the light of the wavelength band illustrated in FIG. 8 by alternately illuminating a first set of LEDs (LEDs emitting B1 light, G1 light, and R1 light) and a second set of LEDs (LEDs emitting UV light, B2 light, and G2 light) among the six LEDs (LEDs that emit the light having wavelength bands of UV, B1, B2, G1, G2, and R1 respectively). Then, 50% of a first set of light (B1 light, G1 light, and R1 light) is reflected in the additional connector (distributor) 200 according to the spectral distribution wavelength characteristics (FIG. 7B), and distributed to the optical paths A and C. In addition, 30% of a second set of light (UV light, B2 light, and G2 light) is reflected in the additional connector (distributor) 200 according to the spectral distribution wavelength characteristics (FIG. 7B), and distributed to the optical paths A and C. In order to make the output intensities of the first set of light and the second set of light uniform, the light intensity in the light source unit 3004 may be adjusted as in the case of generating the white light or the narrow band light. Then, the first medical device and the second medical device are supplied with B1 light, G1 light, and R1 light, and UV light, B2 light, and G2 light at the same timing via the optical path A and the optical path C, respectively.

On the other hand, the second set of light is blocked by the additional connector (distributor) 200 having the spectral distribution wavelength characteristic of FIG. 7B, is not output to the optical path B, and only the first set of light (30% light) passes through the additional connector (distributor) 200 and is intermittently output to the optical path B (that is, light is not output to the optical path B at the timing when the second set of light is supplied to the optical paths A and C). This first set of light (B1 light, G1 light, and R1 light) is output as the white light from the tip of the third medical device, and the image data obtained by imaging the reflected light from the observation target is output as a white light image by performing the process described in FIG. 9.

As described above, the parent endoscope device (first medical device) 101 and the child endoscope device (second medical device) 102 are used as devices for calculating the oxygen saturation, and the grandchild endoscope device (third medical device) 103 can be used as a device for observing white light.

(iii-4) Generation of light used in near-infrared immunotherapy Light used in the near-infrared immunotherapy is output from all the optical paths from optical paths A to C. In this case, the light source unit 3004 emits only the LED that emits the light having the wavelength band R1. Then, 30% of R1 light is reflected in the additional connector (distributor) 200 according to the spectral distribution wavelength characteristics (FIG. 7B), and distributed to the optical paths A and C. On the other hand, 40% of R1 light passes through in the additional connector (distributor) 200 according to the spectral distribution wavelength characteristics (FIG. 7B), and output to the optical path B. The intensity of each R1 light to be output may be adjusted on the light source unit 3004 side, or the gain of the acquired image data may be adjusted by the image processing unit 3008 of the processor 300. In the near-infrared immunotherapy, a cyclic compound named IRDye700 (also known as phthalocyanine), which has a structure in which four phthalimides are cross-linked with nitrogen atoms, is used and has the function of a photoreactive group. The "antibody" has a function of specifically binding to an antigen expressed in cancer cells due to gene mutation and the like. For example, as an antibody of RM-1929 currently in clinical research, "cetuximab" that binds to EGFR (epithelial cell growth factor receptor) is used, and this specifically binds to the antibody. In the near-infrared immunotherapy, when a sufficient time has elapsed after a drug in which an "antibody" and a "photoreactive group" are synthesized in this way is administered (orally or intravenously) to a patient before irradiation with light to bind to a malignant tumor site, the affected area is irradiated with near-infrared light, and the cancer cells to which the drug components are bound burst due to the expansion of the drug components.

(iii-5) ICG (Indocyanine Green) Observation Light Generation

The ICG observation light is output only from the optical paths A and C, and is not output from the optical path B. In this case, the light source unit 3004 emits only the LED that emits the light having the wavelength band R2. Then, 50% of R2 light is reflected in the additional connector (distributor) 200 according to the spectral distribution wavelength characteristics (FIG. 7B), and distributed to the optical paths A and C. On the other hand, R2 light is not output to the optical path B because it does not pass through the additional connector (distributor) 200. The intensity of each R2 light to be output may be adjusted on the light source unit 3004 side, or the gain of the acquired image data may be adjusted by the image processing unit 3008 of the processor 300.

(iv) Other Specific Configuration Examples

Various observation functions can be realized by changing the spectral distribution wavelength characteristics of the additional connector (distributor) 200. FIG. 10 is a diagram illustrating an example (Table 1) of an observation function in a case where the parent endoscope device (first medical device) 101, the child endoscope device (second medical device) 102, and the grandchild endoscope device (third medical device) 103 have the same observation function. For example, since the type of light used (wavelength band) varies depending on the region to be observed (other parts), the ratio of light output from each optical path also varies. Therefore, the operator (user) switches and uses the additional connector (distributor) 200 depending on the area to be observed.

As described above, various observation lights can be output from the additional connector (distributor) 200 by controlling the type and intensity of light incident on the additional connector (distributor) 200 (causing the light source unit 3004 to emit light of which wavelength band and at what intensity). For example, by preparing the additional connector 200 in which the design values of transmission/reflection for each band of the spectroscope are changed, it is possible to adjust the light amount ratio to each device simply by exchanging the additional connector 200. It becomes possible to adjust the allocation of each mode of observation and treatment and the light intensity ratio.

<Others>

As described above, the additional connector (distributor) 200 according to this embodiment may be used for realizing a parent-child scope configured by the parent endoscope device and the child endoscope device or a parent-child-grandchild scope configured by the parent endoscope device, the child endoscope device, and the grandchild endoscope device as described above or, as another example, may be used in a case where a plurality of endoscope devices (the same diameter: sibling scope) are simultaneously inserted in a medical device (or the parent endoscope device) having a plurality of forceps ports (for example, the same diameter) (a multi-lumen type medical device). In addition, in the case of this multi-lumen type medical device, the number of a plurality of medical devices (in this case, endoscope devices) used simultaneously is not limited to three. For example, if the parent endoscope device (first medical device) is a multi-lumen type and has two forceps port channels, five endoscope devices (one parent endoscope device, two child endoscope devices, and two grandchild endoscope devices) in total can be used simultaneously.

The light source included in the light source unit 3004 may include a solid-state light source (LED (Light Emitting Diode) or LD (Laser Diode)), or a discharge lamp (xenon lamp, HID (High-Intensity Discharge) lamp, halogen lamp, etc.).

It should be noted that a plurality of monitors may be prepared and the images captured by the endoscope devices 101 to 103 may be displayed on each monitor, or the display screen of the monitor may be divided into a plurality of areas and the images captured by the endoscope devices 101 to 103 may be displayed in each display area.

<Specific Matters of the Present Disclosure>

(1) Specific Matter 1

An optical distribution connector (additional connector (distributor)), including:

an optical connector portion that is configured to be attachable to and detachable from a processor and realizes an optical connection with the processor;

a plurality of medical device mounting portions, each of which is attachable to and detachable from a medical device; and at least one optical element that distributes light emitted from a light source included in the processor in each direction of the plurality of medical device mounting portions.

With this configuration, it is not necessary to provide a light source device corresponding to each medical device (endoscope device), and the scale of the endoscope system can be reduced.

(2) Specific Matter 2

The optical distribution connector according to Specific matter 1, in which the at least one optical element has a spectral distribution wavelength characteristic defined by light transmittance and light reflectance with respect to each of a plurality of wavelength bands of light.

With this configuration, if the type and intensity of the light output from the light source of the processor are controlled, various observation functions (for example, white light observation mode, narrow band light observation mode, oxygen saturation observation mode, near-infrared immunotherapy mode, and ICG observation mode) can be realized only by mounting one optical distribution connector to the processor and mounting a plurality of medical devices (endoscope devices) to the optical distribution connector. Further, it is possible to easily realize other observation functions by changing the spectral distribution wavelength characteristic.

(3) Specific Matter 3

The optical distribution connector according to Specific matter 1 or 2, in which the optical element is configured by a half mirror or a dichroic mirror.

(4) Specific Matter 4

The optical distribution connector according to Specific matter 1 or 2, in which the optical element is configured by a cross prism.

(5) Specific Matter 5

An endoscope system, including:

a plurality of endoscope devices;

a processor that processes image data captured by the endoscope device to display an image corresponding to the image data to a display device; and an optical distribution connector that is configured to be attachable to and detachable from the plurality of endoscope devices and the processor, and realizes optical connection with the plurality of endoscope devices and the processor, in which the optical distribution connector includes an optical connector portion that is configured to be attachable to and detachable from the processor to realize optical connection with the processor, a plurality of endoscope mounting portions, each of which is attachable to and detachable from the endoscope device, and at least one optical element that distributes light emitted from a light source included in the processor in each direction of the plurality of endoscope mounting portions.

With this configuration, it is not necessary to provide a light source device corresponding to each endoscope device, and the scale of the endoscope system can be reduced.

(6) Specific Matter 6

The endoscope system according to Specific matter 5, in which the at least one optical element has a spectral distribution wavelength characteristic defined by light transmittance and light reflectance with respect to each of a plurality of wavelength bands of light.

With this configuration, if the type and intensity of the light output from the light source of the processor are controlled, various observation functions (for example, white light observation mode, narrow band light observation mode, oxygen saturation observation mode, near-infrared immunotherapy mode, and ICG observation mode) can be realized. Further, it is possible to easily realize other observation functions by changing the spectral distribution wavelength characteristic.

(7) Specific Matter 7

The endoscope system according to Specific matter 5 or 6, in which the optical element includes at least one of a half mirror and a dichroic mirror.

(8) Specific Matter 8

The endoscope system according to Specific matter 5 or 6, in which the optical element is configured by a cross prism.

(9) Specific Matter 9

The endoscope system according to Specific matter 6, in which the processor includes a light source that emits light of a plurality of types of wavelength bands, an operation unit to which an instruction for controlling an operation of the processor is input, and a control unit that controls an intensity of light generated from the light source in response to an instruction input from the operation unit, and the instruction indicates a type of light in a wavelength band and an intensity of light in each wavelength band, which correspond to a desired observation function, and the control unit causes the light source to emit light in a designated wavelength band at a designated intensity in response to the instruction.

In this way, since the control of the light source is performed based on the instruction input by the operator, the optical distribution connector (additional connector (distributor)) is provided with spectral distribution wavelength characteristics capable of realizing the observation mode desired by the operator, so that the observation mode can be easily realized. Further, when another observation mode is not possible to be realized by the same optical distribution connector, the other observation mode can be easily realized by changing to an optical distribution connector having another spectral distribution wavelength characteristic.

(10) Specific Matter 10

The endoscope system according to Specific matter 9, in which the optical distribution connector includes an optical element that distributes and outputs incident light in three directions, and a spectral distribution wavelength characteristic of the optical element is a characteristic in which B1 light, G1 light, and R1 light are transmitted in a first direction by a predetermined ratio, UV light, B2 light, G2 light, and R2 light are not transmitted in the first direction, and UV light, B1 light, B2 light, G1 light, G2 light, R1 light, and R2 light are reflected in each of second and third directions in a predetermined ratio.

(11) Specific Matter 11

The endoscope system according to Specific matter 10, in which, when the desired observation function is a white light observation mode, the control unit causes the light source to output UV light, B1 light, B2 light, G1 light, G2 light, and R1 light of a predetermined intensity in response to the instruction.

(12) Specific Matter 12

The endoscope system according to Specific matter 10, in which, when the desired observation function is a narrow band light observation mode, the control unit causes the light source to output only UV light and G2 light of a predetermined intensity in response to the instruction.

(13) Specific Matter 13

The endoscope system according to Specific matter 10, in which, when the desired observation function is an oxygen saturation observation mode, the control unit controls the light source in response to the instruction such that a first light group configured by B1 light, G1 light, and R1 light of a predetermined intensity and a second light group configured by UV light, B2 light, and G2 light of a predetermined intensity are output alternately.

(14) Specific Matter 14

The endoscope system according to Specific matter 10, in which, when the desired observation function is a near-infrared immunotherapy mode, the control unit causes the light source to output only R1 light of a predetermined intensity in response to the instruction.

(15) Specific Matter 15

The endoscope system according to Specific matter 10, in which, when the desired observation function is an ICG observation mode, the control unit causes the light source to output only R2 light of a predetermined intensity in response to the instruction.

The observation modes described in Specific matters 11 to 15 are merely examples, and the optical distribution connector according to this embodiment can be used in modes other than the observation modes listed in this embodiment.

REFERENCE SIGNS LIST

1 endoscope system
101 parent endoscope device (first medical device)
102 child endoscope device (second medical device)
103 grandchild endoscope device (third medical device)
200 additional connector (distributor)
300 processor
400 monitor
201, 202, 203 connecting portion
204 pin type connector (male)
211, 221, 222 dichroic mirror
231 cross prism
3001 system controller
3004 light source unit
3006 operation panel

The invention claimed is:

1. An endoscope system comprising:

a plurality of endoscope devices;

a processor that processes image data captured by an endoscope device of the plurality of endoscope devices to display an image corresponding to the image data to a display device; and an optical distribution connector that is configured to be attachable to and detachable from the plurality of endoscope devices and the processor, and realizes optical connection with the plurality of endoscope devices and the processor, wherein the optical distribution connector includes:

an optical connector portion that is configured to be attachable to and detachable from the processor to realize optical connection with the processor, a plurality of endoscope mounting portions, each of which is attachable to and detachable from a said endoscope device of the plurality of endoscope devices, and at least one optical element that distributes light emitted from a light source included in the processor in each direction of the plurality of endoscope mounting portions, wherein the at least one optical element has a spectral distribution wavelength characteristic defined by light transmittance and light reflectance with respect to each of a plurality of wavelength bands of light, wherein the processor includes:

a light source that emits light of a plurality of types of wavelength bands;

an operation unit to which an instruction for controlling an operation of the processor is input; and a control unit that controls an intensity of light generated from the light source in response to an instruction input from the operation unit, wherein the instruction indicates a type of light in a wavelength band and an intensity of light in each wavelength band, which correspond to a desired observation function, and wherein the control unit causes the light source to emit light in a designated wavelength band at a designated intensity in response to the instruction, wherein the optical distribution connector includes an optical element that distributes and outputs incident light in three directions, and wherein a spectral distribution wavelength characteristic of the optical element is a characteristic in which B1 light, G1 light, and R1 light are transmitted in a first direction by a first predetermined ratio, UV light, B2 light, G2 light, and R2 light are not transmitted in the first direction, and UV light, B1 light, B2 light, G1 light, G2 light, R1 light, and R2 light are reflected in each of second and third directions in a second predetermined ratio, wherein:

R1 light includes one or more wavelengths that are shorter than one or more wavelengths of R2 light, G1 light includes one or more wavelengths that are shorter than one or more wavelengths of G2 light, R1 light and R2 light, and B1 light includes one or more wavelengths that are shorter than one or more wavelengths of B2 light, G1 light, G2 light, R1 light and R2 light.

2. The endoscope system according to claim 1, wherein, when the desired observation function is a white light observation mode, the control unit causes the light source to output UV light, B1 light, B2 light, G1 light, G2 light, and R1 light of a predetermined intensity in response to the instruction.

3. The endoscope system according to claim 1, wherein, when the desired observation function is a narrow band light observation mode, the control unit causes the light source to output only UV light and G2 light of a predetermined intensity in response to the instruction.

4. The endoscope system according to claim 1, wherein, when the desired observation function is an oxygen saturation observation mode, the control unit controls the light source in response to the instruction such that a first light group configured by B1 light, G1 light, and R1 light of a first predetermined intensity and a second light group configured by UV light, B2 light, and G2 light of a second predetermined intensity are output alternately.

5. The endoscope system according to claim 1, wherein, when the desired observation function is a near-infrared immunotherapy mode, the control unit causes the light source to output only R1 light of a predetermined intensity in response to the instruction.

6. The endoscope system according to claim 1, wherein, when the desired observation function is an ICG observation mode, the control unit causes the light source to output only R2 light of a predetermined intensity in response to the instruction.

* * * * *